US008578942B2

(12) United States Patent
Schennum

(10) Patent No.: US 8,578,942 B2
(45) Date of Patent: Nov. 12, 2013

(54) AEROSOL GENERATOR

(75) Inventor: Steven Michael Schennum, Plainfield, IL (US)

(73) Assignee: British American Tobacco (Investments) Limited, London (GB)

( * ) Notice: Subject to any disclaimer, the term of this patent is extended or adjusted under 35 U.S.C. 154(b) by 617 days.

(21) Appl. No.: 12/787,271

(22) Filed: May 25, 2010

(65) Prior Publication Data

US 2011/0290268 A1 Dec. 1, 2011

(51) Int. Cl.
*A24F 47/00* (2006.01)

(52) U.S. Cl.
USPC .......................................... 131/271; 131/270

(58) Field of Classification Search
None
See application file for complete search history.

(56) References Cited

U.S. PATENT DOCUMENTS

| | | | | |
|---|---|---|---|---|
| 3,425,414 | A | 2/1969 | LaRoche | |
| 4,171,000 | A | 10/1979 | Uhle | |
| 4,223,804 | A * | 9/1980 | Morris et al. | 222/3 |
| 4,393,884 | A | 7/1983 | Jacobs | |
| 4,945,929 | A | 8/1990 | Egilmex | |
| 6,026,990 | A * | 2/2000 | Brunswig | 222/153.13 |
| 2004/0000306 | A1 | 1/2004 | Stradella | |

FOREIGN PATENT DOCUMENTS

| | | | |
|---|---|---|---|
| EP | 1 170 061 | A2 | 1/2002 |
| EP | 1237610 | B1 | 5/2006 |
| GB | 2266466 | A | 11/1993 |
| WO | WO 00/12162 | A1 | 3/2000 |
| WO | WO 00/53247 | A1 | 9/2000 |
| WO | WO 02/100469 | A2 | 12/2002 |
| WO | 2005/044354 | A1 | 5/2005 |
| WO | WO 2009/024578 | A2 | 2/2009 |
| WO | 2009/135729 | A1 | 11/2009 |
| WO | WO 2011/015825 | | 2/2011 |

OTHER PUBLICATIONS

International Search Report and Written Opinion, mailed Aug. 16, 2011, for PCT International Application No. PCT/EP2011/057603, filed May 11, 2011.
International Preliminary Report on Patentability, mailed Aug. 10, 2012, for PCT International Application No. PCT/EP2011/057603, filed May 11, 2011.
International Search Report and Written Opinion, mailed Aug. 25, 2011, for PCT International Application No. PCT/EP2011/057693, filed May 12, 2011.

(Continued)

*Primary Examiner* — Michael J Felton
(74) *Attorney, Agent, or Firm* — N W Poulsen

(57) ABSTRACT

An aerosol generator device has an elongate body with an interior passageway extending longitudinally to its mouth end. The device receives an interchangeable, pressurized canister charged with a nicotine containing liquid that is discharged in a metered dose on manual actuation of a button member that causes a valve in the canister to open and discharge through a discharge tube. A sleeve releasably couples the canister to the body. The button member is slidably mounted on the body for reciprocal movement along a trigger axis Y-Y' extending transversely of the longitudinal axis X-X' of the device, and has a manually depressible surface portion and a camming surface portion that drives a slidable nozzle member to press the discharge tube inwardly of the canister to open its valve and release liquid into the nozzle member. Nozzle forms an aerosol from the liquid, which is delivered to the consumer through outlets in the mouth end of the device.

32 Claims, 7 Drawing Sheets

(56) References Cited

OTHER PUBLICATIONS

International Preliminary Report on Patentability, mailed Nov. 2, 2012, for PCT International Application No. PCT/EP2011/057693, filed May 12, 2011.
International Search Report and Written Opinion, mailed Aug. 4, 2011, for PCT International Application No. PCT/EP2011/057797, filed May 13, 2011.
International Preliminary Report on Patentability, mailed Jul. 6, 2012, for PCT International Application No. PCT/EP2011/057797, filed May 13, 2011.
Invitation to Restrict or Pay Additional Fees, mailed Jul. 6, 2012, for PCT International Application No. PCT/EP2011/057797, filed May 13, 2011.
International Search Report and Written Opinion, mailed Aug. 17, 2011, for PCT International Application No, PCT/EP2011/057945, filed May 17, 2011.
International Preliminary Report on Patentability, mailed May 21, 2012, for PCT International Application No. PCT/EP2011/057945, filed May 17, 2011.
Non-Final Office Action, dated Jul. 23, 2012, for U.S. Appl. No. 12/787,259.
Non-Final Office Action, dated Jan. 17, 2013, for U.S. Appl. No. 12/787,259.
Non-Final Office Action, dated Jul. 13, 2012, for U.S. Appl. No. 12/787,258.
Final Office Action, dated Jan. 18, 2013, for U.S. Appl. No. 12/787,258.
Non-Final Office Action, dated Jun. 20, 2012, for U.S. Appl. No. 12/787,257.
Final Office Action, dated Oct. 23, 2012, for U.S. Appl. No. 12/787,257.
Non-Final Office Action dated Sep. 30, 2013, for U.S. Appl. No. 12/787,257, filed May 25, 2010.
Final Office Action, mailed Aug. 13, 2013, for U.S. Appl. No. 12/787,259.

* cited by examiner

AEROSOL GENERATOR

FIELD OF THE INVENTION

This invention relates to an aerosol generator which may be portable and handheld, to deliver aerosol to the mouth of a consumer, for example aerosol containing nicotine.

BACKGROUND

A nicotine dispensing aerosol device is disclosed in U.S. Pat. No. 4,945,929, which simulates a smoking article such as a cigarette, without having to burn tobacco.

SUMMARY OF THE INVENTION

The invention provides an improved aerosol generator device that can be operated manually by a consumer to deliver aerosol, for example to their mouth.

An embodiment of the invention provides an aerosol generator device that includes an elongate body having a proximal mouth end, a distal end and an interior passageway extending longitudinally to the mouth end. A coupling to the body is configured for releasably coupling a fluid containing pressurised canister having an axial discharge tube depressible inwardly to open a valve therein to release the fluid through the discharge tube, with the canister and the passageway having a common longitudinal axis. A trigger is mounted on the body to reciprocate along a trigger axis extending transversely of the longitudinal axis, the trigger having a manually depressible surface portion facing outwardly of the body, and a camming surface portion operable on depression of the manually depressible surface portion inwardly of the body along the trigger axis, to press the discharge tube inwardly of the canister and operate the valve so as to release fluid from the canister through the discharge tube and through the body to the mouth end.

A tubular nozzle member may be slidably mounted in the body, the nozzle member having an end to abut the tube of the canister and a trigger engaging end that engages the camming surface portion of the trigger so that said inward depression of the trigger drives the nozzle member towards the distal end of the body member to drive the discharge tube inwardly of the canister to operate the valve and release the fluid through the tube and the nozzle.

The body may have a generally tubular sidewall, the interior passageway extending from the distal end to the mouth end, and a trigger chamber extending outwardly from the interior passageway into the sidewall, the trigger being slidably mounted in the trigger chamber for reciprocal movement along the trigger axis, with the depressible surface portion of the trigger being disposed adjacent the exterior surface of the body member.

The coupling may include a sleeve adapted to grip the canister at one end and releasably attached to the distal end of the body at the other end.

The trigger may comprise a manually depressible button, and the body can comprise a generally cylindrical button housing and a generally cylindrical mouth end attached thereto, the button being mounted in the button housing to reciprocate along the trigger axis.

The manually depressible surface portion of the trigger may comprise a cylindrical surface generally coaxial with the button housing. The mouth end may include a filter plug.

The nozzle may include one or more radially extending lugs and the trigger may include one or more depending flanges with an inclined edge that engages a respective lug to provide the camming surface portion.

The canister may be generally cylindrical, with a valve configured to release a metered dose of fluid.

In order that the invention may be more fully understood, embodiments thereof will now be described by way of illustrative example with reference to the accompanying drawings in which:

DETAILED DESCRIPTION

Figure 1:
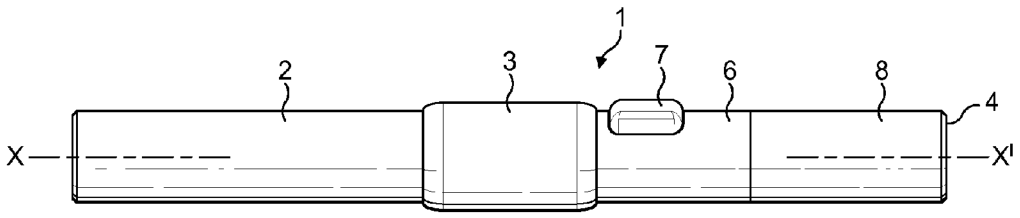
FIG. 1 is side view of an aerosol generator device.
Figure 2:
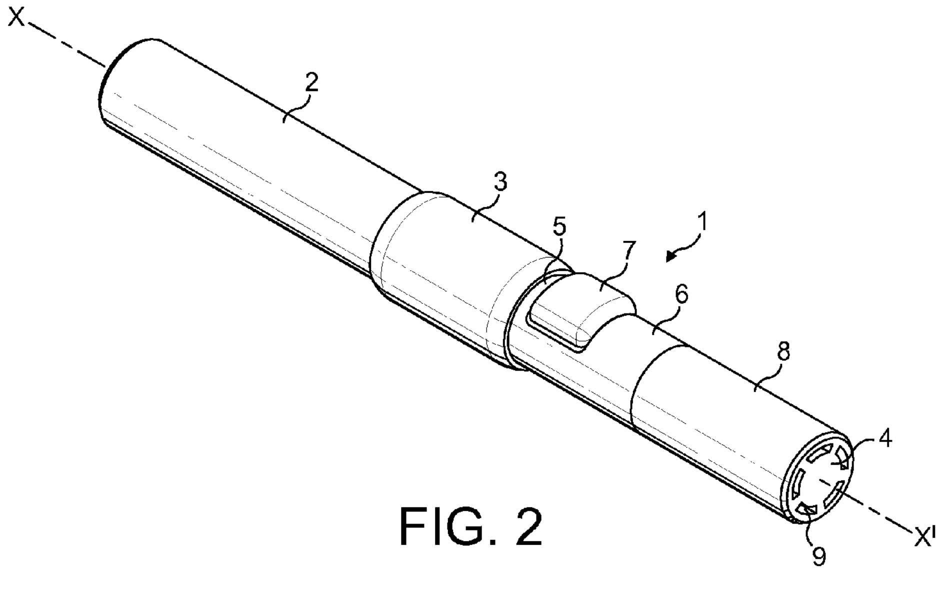
FIG. 2 is a perspective view the aerosol generator device of FIG. 1.

As shown in FIGS. 1 and 2, the aerosol generator device comprises an elongate, generally tubular body 1, with a longitudinal axis X-X', which receives an interchangeable, vessel comprising a generally cylindrical, coaxial, pressurised canister 2 that contains a liquid propellant such as HFA 134a and a substance to be provided as a aerosol to the consumer. A coupling sleeve 3 allows the canister 2 to be attached and replaced by another on the body 1 when the contents of the canister have been consumed by the user.

The contents of the canister 2 may comprise a nicotine-containing liquid with or without additional flavourants, so as to simulate a smoking article such as a cigarette although it will be appreciated that other compositions may be provided within the canister 2.

The body 1 has a proximal, mouth end 4 and a distal end 5 to which the canister 2 is attached by the sleeve 3. The body 1 comprises a button housing 6 that receives a trigger in the form of a manually depressible button 7 for actuating the device, and a generally cylindrical, coaxial mouth end housing 8 that delivers an aerosol formed from liquid from the canister 2, to the mouth of the consumer through circumferential outlet slots 9.

The device may be dimensioned to be of a similar size to a conventional smoking article such as a cigarette, so that the mouth end 4 can be received between the lips of the consumer. The mouth end housing 8 may resemble the filter tip of a conventional cigarette visually. The device can be held between the fingers of the consumer's hand and the button 7 operated to dispense a metered dose of aerosol of fluid from the canister 2 into the consumer's mouth.

Figure 3:
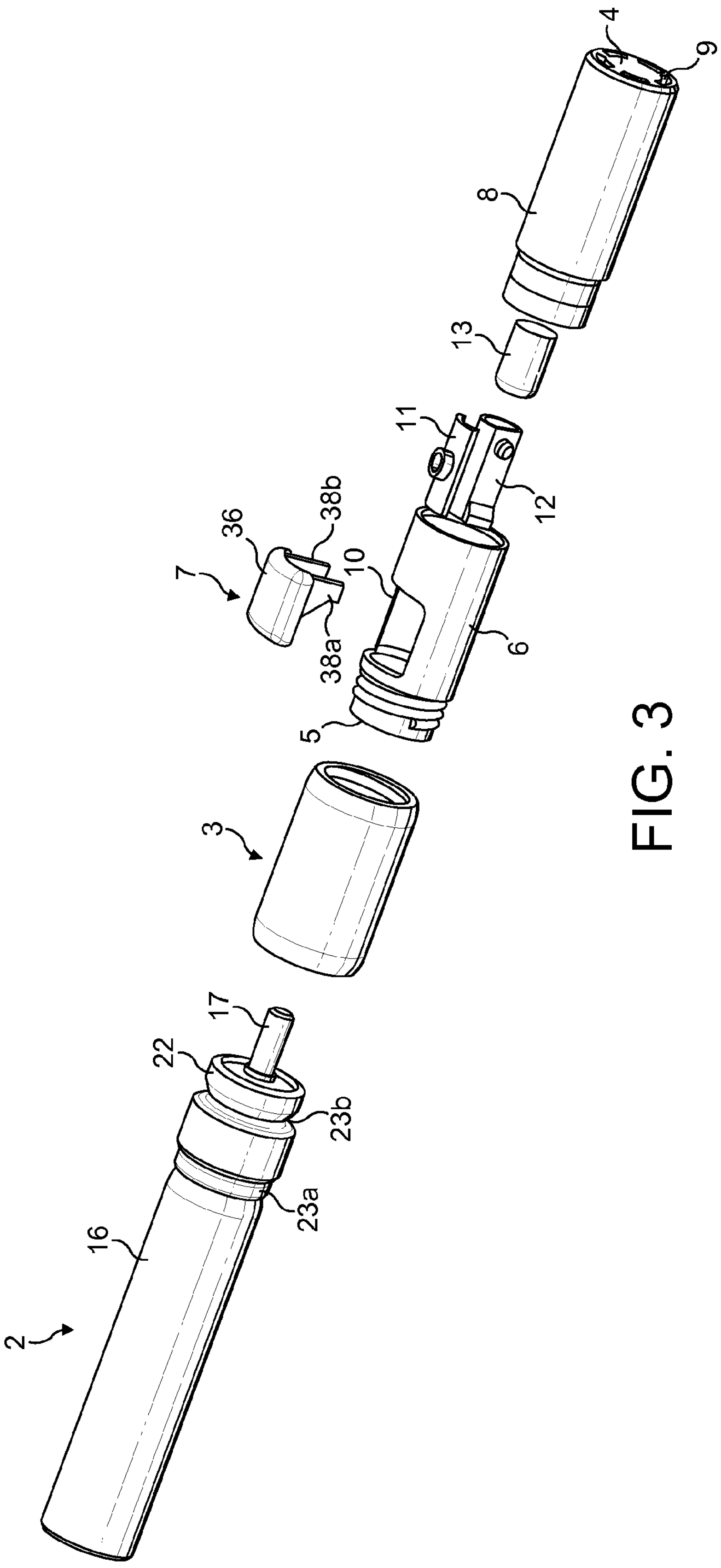
FIG. 3 is an exploded view of the device shown in FIGS. 1 and 2.

As illustrated in the exploded view of FIG. 3, the button housing 6 is generally tubular with a trigger opening 10 through which the button 7 protrudes. The button 7 is retained in the button housing by means of a button retainer strip 11 that is welded, glued or otherwise attached to the underside of the button 7 within the housing 6 to engage the perimeter of the trigger opening 10 on the inside and so limit the travel of the button outwardly, as illustrated in FIGS. 5 and 6.

The button 7 engages a tubular discharge nozzle 12 slidably mounted within the button housing to drive it towards the canister 2 to discharge a metered dose of fluid from the canister, as will be explained in more detail hereinafter.

A filter plug 13 absorbs any excess liquid that may accumulate with multiple actuations of the device. The filter plug 13 may be formed for example of cellulose acetate material and can be arranged coaxially within the mouth end housing 8 to capture larger size droplets in the aerosol emanating from the discharge nozzle, which tend to be discharged at angles closer to the axis of the device than smaller size droplets. It is desirable to supply smaller size droplets to the mouth of the consumer for ease of adsorption and the circumferential disposition of the slots 9 along with the provision the axially disposed filter plug contributes to this outcome. As illustrated in FIG. 4, the filter plug 13 is retained in an inner cylindrical mounting 14 from which extend first and second semi-circular section baffle plates 15 (only one shown in FIG. 4) which tend to direct larger size aerosol droplets towards the filter plug 13 and allow smaller size droplets to pass through the circumferential gap between the cylindrical body of the mouth end housing 8 and the baffle plates 15 to the outlet slots 9 at the mouth end. For further details, reference is directed to the published pamphlet WO 2009/135729 incorporated herein in its entirety by reference.

Referring to FIG. 3, the canister 2 comprises a generally cylindrical canister body 16 that contains a valve with a valve stem in the form of a discharge tube 17 configured so that when pressed axially inwardly of the canister, a metered dose of the pressurised fluid within the canister is discharged through the tube 17 into the nozzle 12.

Figure 7A:
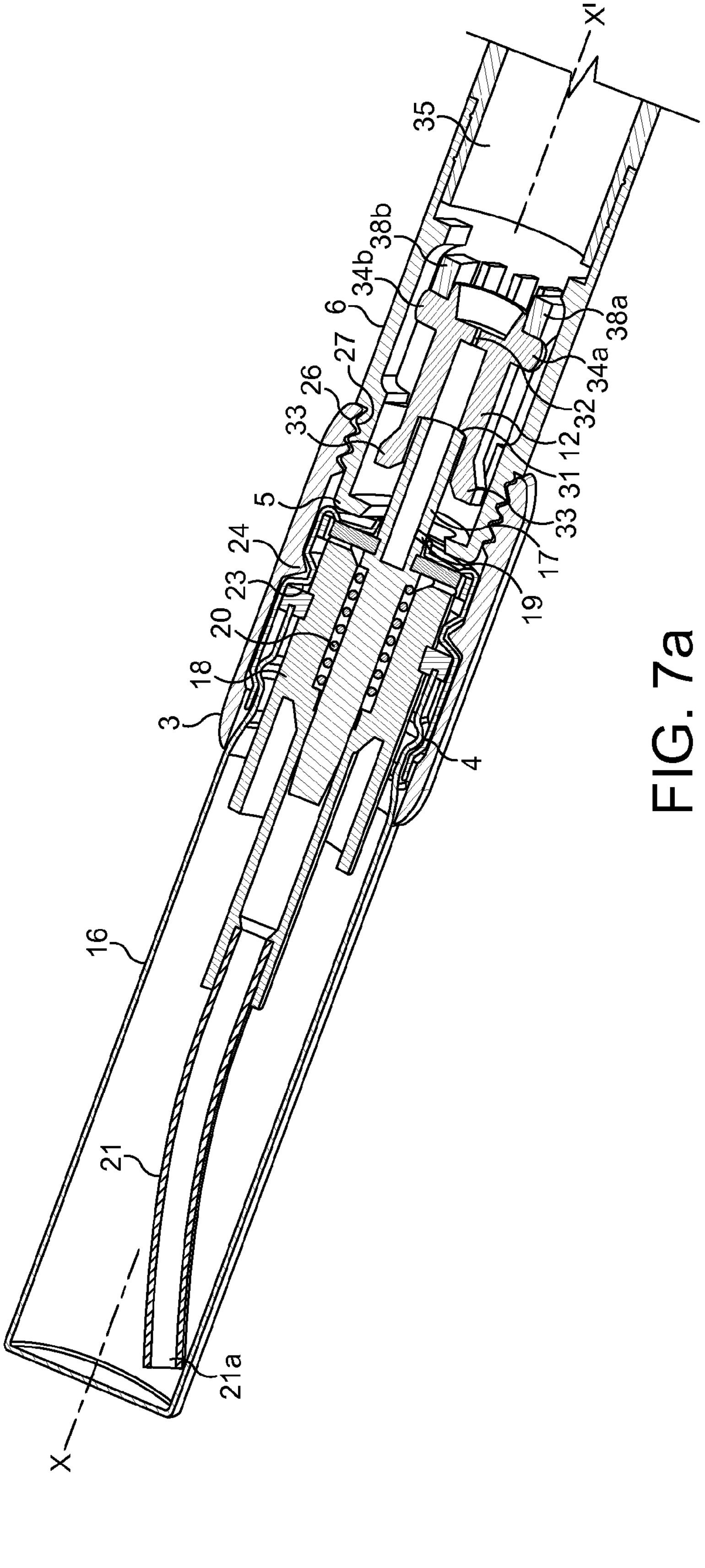
FIGS. 7*a* and 7*b* are partial sectional views showing interior features of the device in the rest and operative discharge configurations respectively.
Figure 7B:
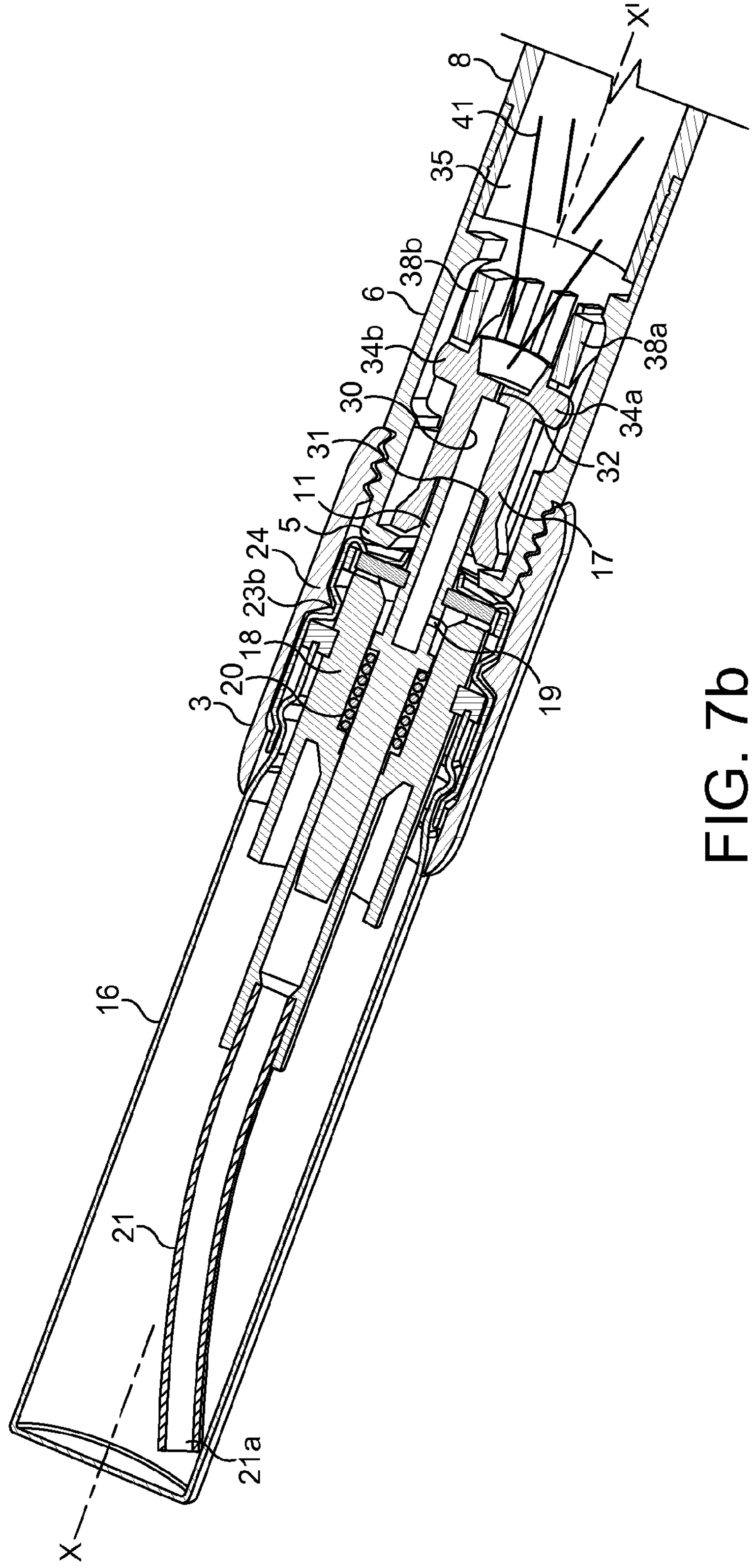

The interior structure of the canister 2 is shown in the sectional views of FIGS. 4 and 7, mounted for operation on the body 1. The canister is mounted with its longitudinal axis aligned with the longitudinal axis X-X' of the device, for dispensing aerosol from the discharge tube 17 into the nozzle 12 towards the mouth end 4. Referring to FIGS. 7*a* and 7*b*, valve 18 in the canister 2 delivers a metered dose of the pressurised contents of the canister through aperture 19 into the discharge tube 17 when it is slid axially inwardly of the canister against the force of spring 20, which urges the tube outwardly to keep the valve 18 normally closed with the aperture disconnected from the interior contents of the canister. A supply pipe 21 feeds the pressurised contents of the canister 2 to the inlet of valve 18 and has a curved end 21*a*.

Figure 8:
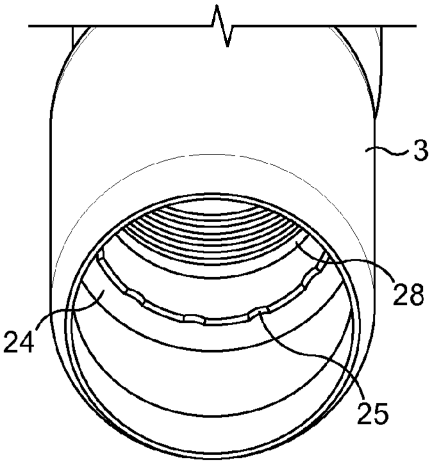
FIG. 8 is a perspective view from one end of a coupling sleeve for attaching a canister to the body of the device.

When fitting a canister 2, it is desirable to arrange its supply pipe 21 so that its curved end 21*a* is directed generally downwardly in use to ensure that substantially all of the liquid contents can be consumed and coupling between the canister and the body is configured for this purpose, as will now be explained. The valve 18 is held in the canister body 16 by a circumferentially crimped ferrule 22. The crimping is arranged in circular grooves 23*a* and 23*b* shown in FIG. 3. Referring to FIG. 8, the coupling sleeve 3 has interior circular lip 24 with radial teeth 25 that is push-fitted onto the canister so that the lip 24 engages in the groove 23*b* and the teeth 24 engage the crimping to prevent rotation of the canister in the coupling sleeve 3. Referring to FIG. 7*a*, the sleeve 3 has a thread 26 on its proximal end that engages with a corresponding thread 27 on the distal end of the button body 6. Referring to FIG. 8, stop 28 is formed on the thread 26 of the coupling sleeve, so that when threadingly engaged fully on the button body, the coupling sleeve 3 and button body 6 adopt a fixed rotational position to one another. By providing a mark on the canister 2 referencing the interior disposition of the inlet supply pipe 21 and a reference mark on the coupling sleeve 3, the canister 2 can be fitted to the sleeve with the marks aligned, so that when the sleeve 3 is screwed onto the body 6, the inlet supply tube extends downwardly when the longitudinal axis X-X' is disposed generally horizontally and button 7 is disposed upwardly.

Figure 9:
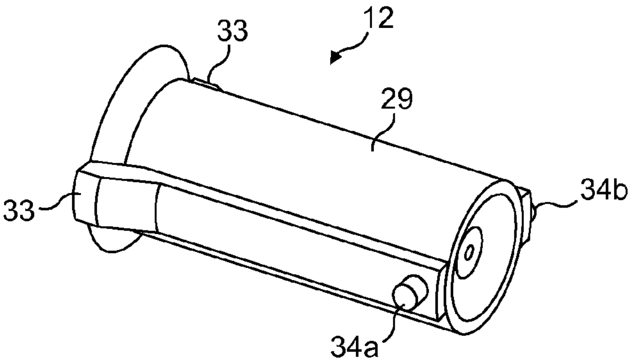
FIG. 9 is a perspective view of the nozzle member of the device.
Figure 10:
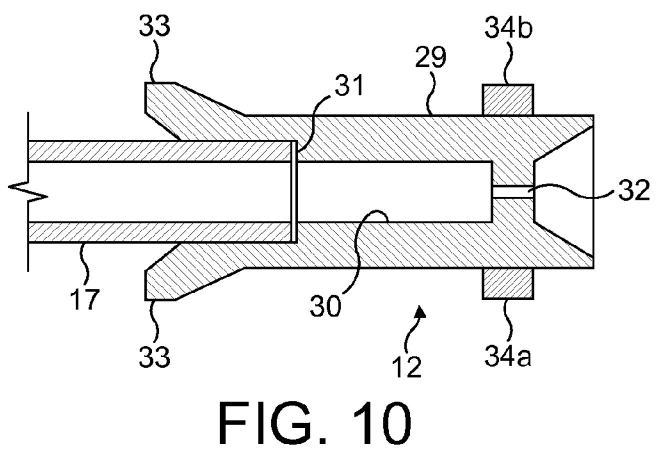
FIG. 10 is a sectional view of the nozzle member.

The nozzle member 12 is illustrated in more detail in FIGS. 9 and 10 and comprises a generally tubular body 29 with an internal axial passageway 30 that comprises a nozzle bore with a step 31 towards is distal end, that engages the discharge tube 17, so that fluid from the canister 2 is discharged from the tube 17 into the passageway 30. The passageway 30 also includes a region of restricted diameter that defines a nozzle 32 to create an aerosol of the contents discharged from the canister 2 into the bore 30, the aerosol being directed into the body 1 towards the mouth end 4.

As shown in FIGS. 9 and 10, the nozzle member 12 includes diametrically opposed flats 33 that are received in corresponding grooves (not shown) in the button housing 6 to prevent rotation of the nozzle member when it moves back and forth. Also, the nozzle member 12 includes first and second diametrically opposed lugs 34*a*, 34*b* which engage with the button member 7 for sliding the nozzle member 12 back and forth axially as described in more detail hereinafter.

As shown in FIGS. 4 and 7, the button housing 6 and the mouth end housing 8 of the body 1 provide an interior passageway 35 extending from the distal end 5 to the mouth end 4. The trigger opening 10 extends through the side wall of the button housing and receives the button member 7 for sliding movement back and forth along a trigger axis Y-Y' shown in FIGS. 5 and 6 orthogonal to the longitudinal axis X-X'.

Figure 5A:
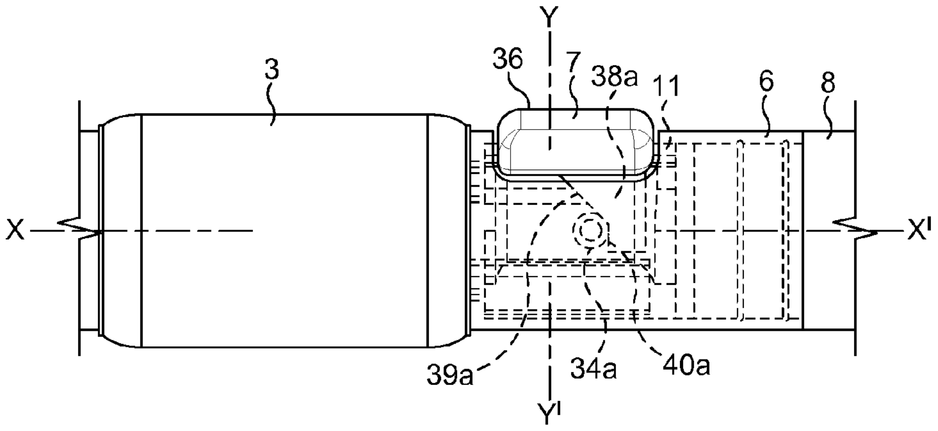
FIGS. 5*a* and 5*b* are partial side views showing interior features of the device in the rest and operative discharge configurations respectively.
Figure 5B:
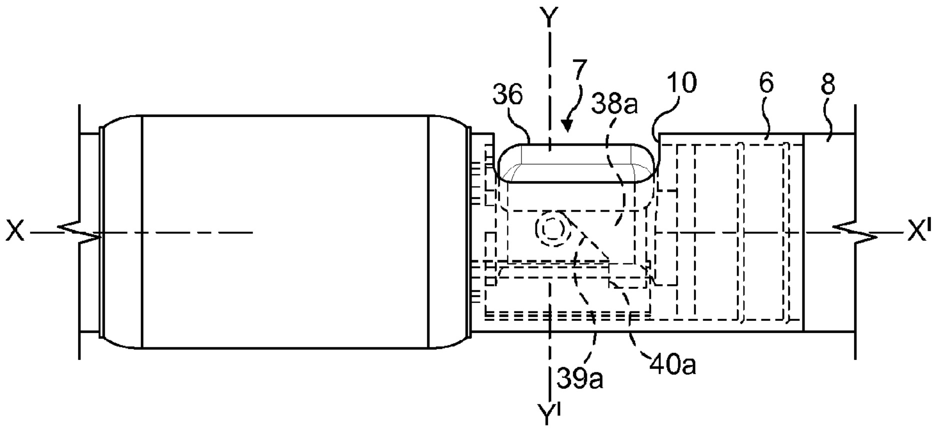
Figure 6A:
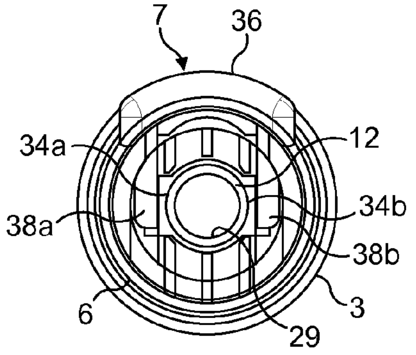
FIGS. 6*a* and 6*b* are sectional views along the line Y-Y' of FIG. 5 in the rest and operative discharge configurations respectively.
Figure 6B:
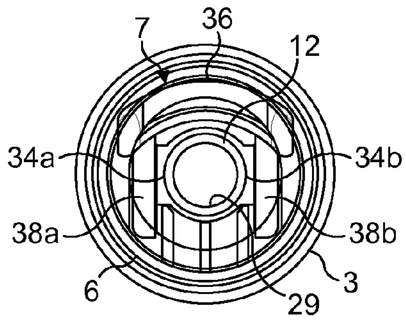

The button member 7 comprises a manually depressible upper surface 36 which is generally part cylindrical and coaxial with the longitudinal axis X-X', and first and second depending flanges 38*a*, 38*b* disposed on opposite sides of the longitudinal axis X-X'. As shown in FIGS. 5 and 6 the flange 38*a* of the button member 6 slidingly engages with the lug 34*a* and 34*b* of the nozzle member 12, and the flange 38*a* has a camming surface portion 39*a* that is inclined to the trigger axis Y-Y' so that as the button member is depressed manually inwardly along the trigger axis Y-Y' against the lug 34*a*, the nozzle member 12 slides towards the canister 2 in the longitudinal axial direction X-X' from a rest position shown in FIGS. 5*a* and 6*a* to discharge position shown in FIGS. 5*b* and 6*b*. The flange 38*a* also has a non-inclined end surface portion 40*a* which engages the lug 34*a* in the rest position shown in FIGS. 5*a* and 6*a*. The arrangement is configured so that the nozzle member 12 is pressed against the force of the spring 20 of the canister 2, with a force that does not open the valve 18 of the canister but provides a pre-compression of the spring which facilitates manual operation of the button member and also resiliently drives the button member outwardly to retain it in the rest position shown, when released by the user.

It will be understood that the flange 38*b* is similarly configured with a camming surface portion 39*b* and end portion 40*b* that engage lug 34*b* on the opposite side of the axis X-X', with the result that axially symmetric forces are applied by the button member 7 to the nozzle member 12.

Figure 4A:
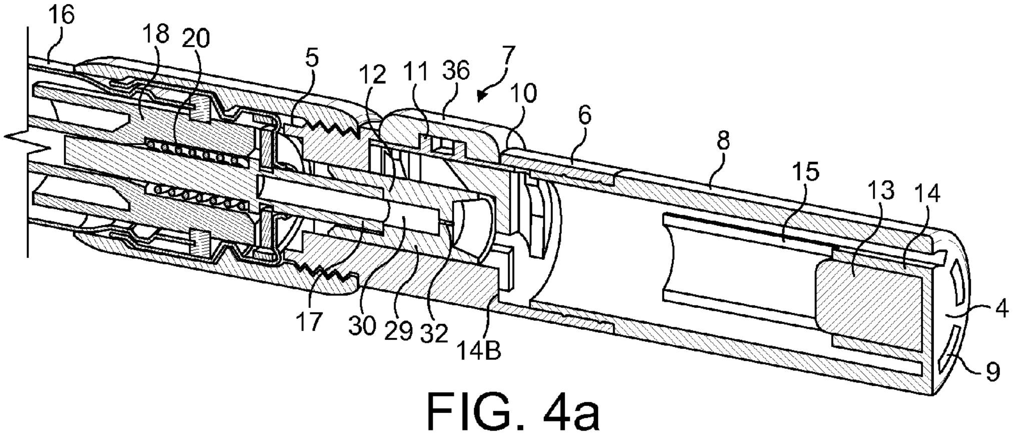
FIG. 4*a* is a partial sectional view of the device shown FIGS. 1 to 3 in a rest configuration FIG. 4*b* corresponds to FIG. 4*a* with the device in an operative, discharge configuration.
Figure 4B:
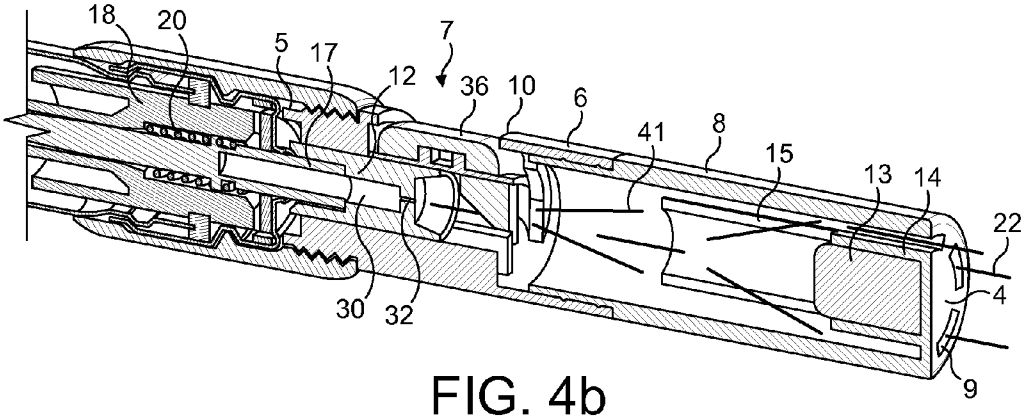

The device is also shown in the rest position and the discharge position in the sectional views of FIGS. 4*a* and 7*a* (rest position) and FIGS. 4*b* and 7*b* (discharge position). It can be seen that when the button member is depressed inwardly, the nozzle member 12 is slid by the button member axially towards the canister 2, so as to depress the discharge tube 17 inwardly of the canister 2 so that the valve 18 releases a metered dose of liquid from the canister 2, which is discharged through the tube 17 into the bore 30 of the nozzle member 12. The liquid passes through nozzle 32 where it is formed into an aerosol 41 that passes into the mouth end housing 8. Larger diameter aerosol droplets tend to be ejected from the nozzle 32 closer to the axial centreline X-X' than smaller diameter droplets and tend to be collected by the filter plug 13, whereas the smaller diameter droplets pass to the outlet slots 9 in the mouth end 4, for consumption by the user.

On release of the button member 7 after the aerosol discharge, it reciprocates along the trigger axis Y-Y' back to the rest position due to the resilience of the spring 20, which drives the discharge tube 17 and the nozzle member 12 away from the canister along the axis X-X', so that the lugs 34*a* and 34*b* and the camming surfaces 39*a* and 39*b* urge the button member 7 to slide outwardly along axis Y-Y'.

Many modifications and variations within the scope of the claimed invention will be evident to those skilled in the art. For example different releasable fixings for the canister on the body may be utilised. In particular, the coupling sleeve may be configured to be more closely aligned with the cylindrical shape of the canister and mouthpiece housing. Also, other fixings may be used such as a bayonet coupling.

Also whilst the described examples of generator device are generally cylindrical with a circular cross section, other cross sectional shapes can be used, such as rectangular or triangular.

Furthermore, although the canister is described as an interchangeable element to allow the supply of liquid to be replenished, an integral pressurised supply vessel may be provided in the device, so that the device can be used multiple times and then discarded once the liquid supply has been exhausted from the vessel. In a modification, an inlet valve may be provided to allow the supply to be replenished from an exterior, pressurised source.

The valve 18 described herein is configured to deliver a metered dose on actuation but instead, a continuous flow valve could be used such that the consumer can maintain a flow of aerosol by continuously depressing the trigger.

The mouth end can be configured differently from that shown in the Figures. For example the mouth end could be a tapered cylindrical shape with flat piece for easy positioning and orientation cue in the mouth. Also, textured or rough finishes can be applied to the exterior surface of the mouthpiece to stimulate sensation in the lips.

The supply tube of the pressurised canister may be of flexible construction and provided with a weighted end as to always assume the lowest position in the canister orientation and allow for complete consumption of the canister contents.

Also, the mouthpiece may be detachable and this may permit the filter plug to be changed.

Other inventive variations and aspects of the disclosure may include other non-limiting embodiments. For example, in one embodiment, an aerosol generator device may comprise an elongate body having a proximal mouth end, a distal end and an interior passageway extending longitudinally to the mouth end, a coupling for releasably coupling to the body, a fluid containing pressurised canister having an axial discharge tube depressible inwardly to open a valve therein to release the fluid through the discharge tube, with the canister and the passageway having a common longitudinal axis, and a trigger mounted on the body to reciprocate along a trigger axis extending transversely of the longitudinal axis, the trigger having a manually depressible surface portion facing outwardly of the body, and a camming surface portion operable on depression of the manually depressible surface portion inwardly of the body along the trigger axis, to press the discharge tube inwardly of the canister and operate the valve so as to release fluid from the canister through the discharge tube and through the body to the mouth end.

In one implementation, the aerosol generator device may include a tubular nozzle member slidably mounted in the body, the nozzle member having an end to abut the tube of the canister and a trigger engaging end that engages the camming surface portion of the trigger so that said inward depression of the trigger drives the nozzle member towards the distal end of the body member to drive the discharge tube inwardly of the canister to operate the valve and release the fluid through the tube and the nozzle.

In one implementation, the body may include a generally tubular sidewall, the interior passageway extending from the distal end to the mouth end, and a trigger opening that extends from the interior passageway through the sidewall, the trigger being slidably mounted in the trigger opening for reciprocal movement along the trigger axis.

In one implementation, the aerosol generator device may include a coupling that includes a sleeve adapted to grip the canister at one end and releasably attached to the distal end of the body at the other end.

In one implementation, the trigger may comprise a manually depressible button, and the body may comprise a generally cylindrical button housing and a generally cylindrical mouth end attached thereto, wherein the button is mounted in the button housing to reciprocate along the trigger axis. In a further implementation, the manually depressible surface portion of the trigger may comprise a cylindrical surface generally coaxial with the button housing.

In one implementation, the mouth end may include a filter plug therein.

In one implementation, the nozzle may include a radially extending lug and the trigger may include a depending flange with an inclined edge that engages the lug to provide the camming surface portion. In one implementation, the aerosol generator may include a further lug on the nozzle, said lugs being disposed diametrically opposite one another, and the trigger may include a further depending flange, said flanges being disposed on opposite sides of the axis of the body to engage the lugs respectively.

In one implementation, the aerosol generator device may include the canister. In a further implementation the canister may be generally cylindrical and may have a valve therein configured to release a metered dose of fluid.

In one implementation, the aerosol generator may have a detachable mouthpiece at the mouth end.

In another embodiment, the aerosol generator device may comprise an elongate body having a proximal mouth end, a distal end and an interior passageway extending longitudinally to the mouth end, a fluid supply vessel for containing pressurised fluid, having a valve and a discharge tube depressible inwardly to open the valve to release fluid through the discharge tube, with the vessel and the passageway having a common longitudinal axis, and a trigger mounted on the body to reciprocate along a trigger axis extending transversely of the longitudinal axis, the trigger having a manually depressible surface portion facing outwardly of the body, and a camming surface portion operable on depression of the manually depressible surface portion inwardly of the body along the trigger axis, to press the discharge tube inwardly of the canister and operate the valve so as to release fluid from the canister through the discharge tube and through the body to the mouth end.

In one implementation, the vessel may be interchangeable.

In one implementation, said fluid may include nicotine and a propellant.

The invention claimed is:

1. An aerosol generator device comprising:

an elongate body having a proximal mouth end, a distal end and an interior passageway extending longitudinally to a mouth end, a coupling for releasably coupling to the body a fluid containing pressurised canister having an axial discharge tube that on inward depression is configured to open a valve therein and release the fluid through the discharge tube, with the canister and the passageway having a common longitudinal axis, a trigger mounted on the body and configured to reciprocate along a trigger axis extending transversely of the longitudinal axis, the trigger having a manually depressible surface portion facing outwardly of the body, and a camming surface portion operable on depression of the manually depressible surface portion inwardly of the body along the trigger axis, such that pressing the discharge tube inwardly of the canister operates the valve such that fluid from the canister is released through the discharge tube and through the body to the mouth end, and a tubular nozzle member slidably mounted in the body, the nozzle member having an end to abut the tube of the canister and a trigger engaging end that engages the camming surface portion of the trigger so that said inward depression of the trigger drives the nozzle member towards the distal end of the body member to drive the discharge tube inwardly of the canister to operate the valve and release the fluid through the tube and the nozzle, wherein the trigger comprises a manually depressible button, and the body comprises a generally cylindrical button housing and a generally cylindrical mouth end attached thereto, wherein the button is mounted in the button housing and is configured to reciprocate along the trigger axis, wherein the manually depressible surface portion of the trigger comprises a cylindrical surface generally coaxial with the button housing, and wherein the mouth end includes a filter plug therein.

2. The aerosol generator device according to claim 1, wherein the body includes a generally tubular sidewall, the interior passageway extending from the distal end to the mouth end, and a trigger opening that extends from the interior passageway through the sidewall, the trigger being slidably mounted in the trigger opening for reciprocal movement along the trigger axis.

3. The aerosol generator device according to claim 1, wherein the coupling includes a sleeve configured to grip the canister at one end and to releasably attach to the distal end of the body at the other end.

4. The aerosol generator device according to claim 1, wherein the nozzle includes a radially extending lug and the trigger includes a depending flange with an inclined edge that engages the lug to provide the camming surface portion.

5. The aerosol generator device according to claim 4, wherein the nozzle includes a second lug, said lugs being disposed diametrically opposite one another, and the trigger includes a second depending flange, said flanges being disposed on opposite sides of the axis of the body to engage the lugs respectively.

6. The aerosol generator device according to claim 1, further comprising the canister coupled to the body.

7. The aerosol generator device according to claim 6, wherein the canister is generally cylindrical and has a valve therein configured to release a metered dose of fluid.

8. The aerosol generator device according to claim 1, further comprising a detachable mouthpiece at the mouth end.

9. The aerosol generator device according to claim 6 wherein the canister contains fluid that includes nicotine and a propellant.

10. An aerosol generator device comprising:

an elongate body having a proximal mouth end, a distal end and an interior passageway extending longitudinally to a mouth end, a coupling for releasably coupling to the body a fluid containing pressurised canister having an axial discharge tube that on inward depression is configured to open a valve therein and release the fluid through the discharge tube, with the canister and the passageway having a common longitudinal axis, a trigger mounted on the body and configured to reciprocate along a trigger axis extending transversely of the longitudinal axis, the trigger having a manually depressible surface portion facing outwardly of the body, and a camming surface portion operable on depression of the manually depressible surface portion inwardly of the body along the trigger axis, such that pressing the discharge tube inwardly of the canister operates the valve such that fluid from the canister is released through the discharge tube and through the body to the mouth end, and a tubular nozzle member slidably mounted in the body, the nozzle member having an end to abut the tube of the canister and a trigger engaging end that engages the camming surface portion of the trigger so that said inward depression of the trigger drives the nozzle member towards the distal end of the body member to drive the discharge tube inwardly of the canister to operate the valve and release the fluid, through the tube and the nozzle, wherein the nozzle includes a radially extending lug and the trigger includes a depending flange with an inclined edge that engages the lug to provide the camming surface portion.

11. The aerosol generator device according to claim 10, wherein the body includes a generally tubular sidewall, the interior passageway extending from the distal end to the mouth end, and a trigger opening that extends from the interior passageway through the sidewall, the trigger being slidably mounted in the trigger opening for reciprocal movement along the trigger axis.

12. The aerosol generator device according to claim 10, wherein the coupling includes a sleeve configured to grip the canister at one end and to releasably attach to the distal end of the body at the other end.

13. The aerosol generator device according to claim 10, wherein the trigger comprises a manually depressible button, and wherein the body comprises a generally cylindrical button housing and a generally cylindrical mouth end attached thereto, wherein the button is mounted in the button housing and is configured to reciprocate along the trigger axis.

14. The aerosol generator device according to claim 13, wherein the manually depressible surface portion of the trigger comprises a cylindrical surface generally coaxial with the button housing.

15. The aerosol generator device according to claim 13, wherein the mouth end includes a filter plug therein.

16. The aerosol generator device according to claim 10, wherein the nozzle includes a second lug, said lugs being disposed diametrically opposite one another, and the trigger includes a second depending flange, said flanges being disposed on opposite sides of the axis of the body to engage the lugs respectively.

17. The aerosol generator device according to claim 10, further comprising the canister coupled to the body.

18. The aerosol generator device according to claim 10, wherein the canister is generally cylindrical and has a valve therein configured to release a metered dose of fluid.

19. The aerosol generator device according to claim 10, further comprising a detachable mouthpiece at the mouth end.

20. The aerosol generator device according to claim 14, wherein the canister contains fluid that includes nicotine and a propellant.

21. An aerosol generator device for dispensing aerosol to the mouth of a user, comprising:

an elongate body having a proximal mouth end receivable in the mouth of a user, a distal end and an interior passageway extending longitudinally to a mouth end, a coupling for releasably coupling to the body, a fluid containing pressurised canister having an axial discharge tube that on inward depression is configured to open a valve therein and release the fluid through the discharge tube, with the canister and the passageway having a common longitudinal axis, a trigger mounted on the body and configured to reciprocate back and forth along a trigger axis extending transversely of the longitudinal axis, the trigger having a manually depressible surface portion facing outwardly of the body, and a camming surface portion operable on depression of the manually depressible surface portion inwardly of the body along the trigger axis to cause pressing of the discharge tube inwardly of the canister to operate the valve and release fluid from the canister through the discharge tube and through the body for dispensing through the mouth end to the mouth of the user, and a tubular nozzle member slidably mounted in the body, the nozzle member having an end to abut the tube of the canister and a trigger engaging end that slidingly engages the camming surface portion of the trigger so that said inward depression of the trigger drives the nozzle member towards the distal end of the body member to drive the discharge tube inwardly of the canister to operate the valve and release the fluid through the discharge tube and the nozzle member.

22. The aerosol generator device according to claim 21, wherein the body includes a generally tubular sidewall, the interior passageway extending from the distal end to the mouth end, and a trigger opening that extends from the interior passageway through the sidewall, the trigger being slidably mounted in the trigger opening for reciprocal movement along the trigger axis.

23. The aerosol generator device according to claim 21, wherein the coupling includes a sleeve configured to grip the canister at one end and to releasably attach to the distal end of the body at the other end.

24. The aerosol generator device according to claim 21, wherein the trigger comprises a manually depressible button, and wherein the body comprises a generally cylindrical button housing and a generally cylindrical mouth end attached thereto, wherein the button is mounted in the button housing and is configured to reciprocate along the trigger axis.

25. The aerosol generator device according to claim 24, wherein the manually depressible surface portion of the trigger comprises a cylindrical surface generally coaxial with the button housing.

26. The aerosol generator device according to claim 21, wherein the mouth end includes a filter plug therein.

27. The aerosol generator device according to claim 21, wherein the nozzle includes a radially extending lug and the trigger includes a depending flange with an inclined edge that engages the lug to provide the camming surface portion.

28. The aerosol generator device according to claim 27, wherein the nozzle includes a second lug, said lugs being disposed diametrically opposite one another, and the trigger includes a second depending flange, said flanges being disposed on opposite sides of the axis of the body to engage the lugs respectively.

29. The aerosol generator device according to claim 21, further comprising the canister coupled to the body.

30. The aerosol generator device according to claim 29, wherein the canister is generally cylindrical and has a valve therein configured to release a metered dose of fluid.

31. The aerosol generator device according to claim 21, further comprising a detachable mouthpiece at the mouth end.

32. The aerosol generator device according to claim 29, wherein the canister contains fluid that includes nicotine and a propellant.

* * * * *